US010039876B2

(12) United States Patent
Maculan et al.

(10) Patent No.: US 10,039,876 B2
(45) Date of Patent: Aug. 7, 2018

(54) SYSTEM FOR REMOVING UNDESIRABLE ELEMENTS FROM BLOOD USING A FIRST WASH STEP AND A SECOND WASH STEP

(71) Applicant: Sorin Group Italia S.r.l., Milan (IT)

(72) Inventors: Elisa Maculan, Gallarate (IT); Laura Scholze, Munich (DE)

(73) Assignee: Sorin Group Italia S.r.l., Milan (IT)

( * ) Notice: Subject to any disclaimer, the term of this patent is extended or adjusted under 35 U.S.C. 154(b) by 365 days.

(21) Appl. No.: 14/266,537

(22) Filed: Apr. 30, 2014

(65) Prior Publication Data
US 2015/0314060 A1 Nov. 5, 2015

(51) Int. Cl.
| A61M 1/36 | (2006.01) |
| A61M 1/02 | (2006.01) |
| A61M 1/38 | (2006.01) |
| B04B 1/08 | (2006.01) |
| B04B 5/10 | (2006.01) |
| B04B 13/00 | (2006.01) |

(52) U.S. Cl.
CPC ........ *A61M 1/3693* (2013.01); *A61M 1/0272* (2013.01); *A61M 1/3692* (2014.02); *A61M 1/3696* (2014.02); *A61M 1/38* (2013.01); *A61M 2202/08* (2013.01); *B04B 1/08* (2013.01); *B04B 5/10* (2013.01); *B04B 13/00* (2013.01)

(58) Field of Classification Search
CPC .... A61M 1/3692; A61M 1/3693; A61M 1/38; A61M 1/382; B04B 1/08; B04B 5/10; B04B 13/00
USPC ................................................ 494/2, 27, 37
See application file for complete search history.

(56) References Cited

U.S. PATENT DOCUMENTS

| 1,385,306 A | 7/1921 | Clayton |
| 2,835,517 A | 5/1958 | Beerli |

(Continued)

FOREIGN PATENT DOCUMENTS

| BR | 102014011278 A2 | 2/2016 | |
| EP | 0682953 A1 * | 11/1995 | .............. A61M 1/02 |

(Continued)

OTHER PUBLICATIONS

European Search Report issued in EP Application No. 06124795, dated May 11, 2007, 8 pages.

(Continued)

*Primary Examiner* — Walter D Griffin
*Assistant Examiner* — Shuyi S Liu
(74) *Attorney, Agent, or Firm* — Faegre Baker Daniels LLP

(57) ABSTRACT

A system for removing undesirable elements from blood. The system includes a centrifuge bowl to separate the blood into components according to relative densities of the components, a pump to provide wash solution that washes the blood in the centrifuge bowl, and a controller to wash the blood in the centrifuge bowl in a first wash and remove first undesirable elements and to wash the blood in the centrifuge bowl in a second wash and remove trapped undesirable elements. The controller to further mix the blood and the wash solution in the centrifuge bowl and provide diluted blood, separate the diluted blood into concentrated blood and the wash solution, fill the centrifuge bowl with previously concentrated blood to build a buffy coat, and empty the centrifuge bowl of the concentrated blood and the previously concentrated blood after the buffy coat is reached.

14 Claims, 11 Drawing Sheets

(56) References Cited

U.S. PATENT DOCUMENTS

| | | |
|---|---|---|
| 3,317,127 A | 5/1967 | Cole |
| 3,409,213 A | 11/1968 | Latham, Jr. |
| 3,519,201 A | 7/1970 | Eisel et al. |
| 3,565,330 A | 2/1971 | Latham, Jr. |
| 3,581,981 A | 6/1971 | Latham, Jr. |
| 3,785,549 A | 1/1974 | Latham, Jr. |
| 4,140,268 A | 2/1979 | Lacour |
| 4,668,214 A * | 5/1987 | Reeder .............. A61M 1/3621 494/27 |
| 4,718,888 A | 1/1988 | Darnell |
| 4,795,419 A | 1/1989 | Yawn et al. |
| 4,838,849 A | 6/1989 | Calari |
| 4,889,524 A | 12/1989 | Fell et al. |
| 4,919,817 A | 4/1990 | Schoendorfer et al. |
| 5,060,957 A | 10/1991 | Stolzenberg et al. |
| 5,062,826 A | 11/1991 | Mantovani et al. |
| 5,104,372 A | 4/1992 | Rossetto |
| 5,288,088 A | 2/1994 | Santandrea et al. |
| 5,298,171 A | 3/1994 | Biesel |
| 5,311,908 A | 5/1994 | Barone et al. |
| 5,312,319 A | 5/1994 | Salter |
| 5,379,775 A | 1/1995 | Kruse |
| 5,383,911 A | 1/1995 | Mann |
| 5,385,539 A | 1/1995 | Maynard |
| 5,387,174 A | 2/1995 | Rochat |
| 5,417,715 A | 5/1995 | Noren et al. |
| 5,423,738 A | 6/1995 | Robinson et al. |
| 5,478,479 A | 12/1995 | Herrig |
| 5,505,683 A | 4/1996 | Geringer et al. |
| 5,514,070 A | 5/1996 | Pages |
| 5,591,113 A | 1/1997 | Darnell et al. |
| 5,607,579 A | 3/1997 | Latham, Jr. et al. |
| 5,658,231 A | 8/1997 | Schmitt et al. |
| 5,730,883 A | 3/1998 | Brown |
| 5,851,169 A | 12/1998 | Meresz et al. |
| 5,873,810 A | 2/1999 | Holm et al. |
| 5,876,611 A | 3/1999 | Shettigar |
| 5,919,125 A | 7/1999 | Berch |
| 5,964,690 A | 10/1999 | Patton et al. |
| 6,241,649 B1 | 6/2001 | Zanella et al. |
| 6,299,784 B1 | 10/2001 | Biesel |
| 6,348,031 B1 | 2/2002 | Unger et al. |
| 6,352,499 B1 | 3/2002 | Geigle |
| 6,416,456 B2 | 7/2002 | Zanella et al. |
| 6,605,028 B2 | 8/2003 | Dolecek |
| 6,629,919 B2 | 10/2003 | Egozy et al. |
| 6,716,151 B2 | 4/2004 | Panzani et al. |
| 7,001,323 B2 | 2/2006 | Panzani et al. |
| 7,211,037 B2 | 5/2007 | Briggs et al. |
| 7,452,322 B2 | 11/2008 | Headley et al. |
| 7,993,257 B2 | 8/2011 | Simonini et al. |
| 8,262,552 B2 | 9/2012 | Simonini et al. |
| 2003/0181305 A1 | 9/2003 | Briggs et al. |
| 2005/0054508 A1 | 3/2005 | Panzani et al. |
| 2006/0040818 A1 | 2/2006 | Jorgensen et al. |
| 2007/0213191 A1 | 9/2007 | Chammas |
| 2008/0124700 A1 | 5/2008 | Fortini et al. |
| 2008/0128367 A1 | 6/2008 | Rochat |
| 2008/0132397 A1 | 6/2008 | Rochat |
| 2008/0153686 A1 | 6/2008 | Rochat |
| 2008/0264841 A1 | 10/2008 | Rochat |
| 2009/0050579 A1 | 2/2009 | Rochat et al. |
| 2009/0065424 A1 | 3/2009 | Rochat |
| 2009/0305863 A1 | 12/2009 | Simonini et al. |
| 2011/0237418 A1 | 9/2011 | Chammas |
| 2011/0256999 A1 | 10/2011 | Simonini et al. |
| 2012/0065047 A1* | 3/2012 | Chapman .............. B01L 3/5021 494/16 |
| 2012/0225419 A1* | 9/2012 | Min .................... A61M 1/3693 435/2 |
| 2013/0017943 A1* | 1/2013 | Toi .......................... B04B 11/02 494/2 |
| 2013/0079211 A1 | 3/2013 | Simonini et al. |
| 2013/0331815 A1 | 12/2013 | Fortini et al. |
| 2014/0045672 A1 | 2/2014 | Galavotti et al. |

FOREIGN PATENT DOCUMENTS

| | | |
|---|---|---|
| EP | 0931554 A2 | 7/1999 |
| EP | 1254675 A1 | 11/2002 |
| EP | 1512419 B1 | 3/2005 |
| EP | 2138237 B1 | 12/2009 |
| JP | H08509403 A | 10/1996 |
| JP | 09164343 A | 6/1997 |
| JP | 9192215 A | 7/1997 |
| JP | H09187504 A | 7/1997 |
| JP | 2003334067 A | 11/2003 |
| JP | 2005081087 A | 3/2005 |
| JP | 2009101187 A | 5/2009 |
| JP | 2009207521 A | 9/2009 |
| JP | 2009291335 A | 12/2009 |
| JP | 2010042398 A | 2/2010 |
| WO | 1980001470 A1 | 7/1980 |
| WO | WO1998029149 A1 | 7/1998 |
| WO | WO2007095771 A1 | 8/2007 |
| WO | WO2007098623 A1 | 9/2007 |
| WO | WO 2010064538 A1 * | 6/2010 .......... A61M 1/0209 |

OTHER PUBLICATIONS

Gilbert et al., "Hematocrit Monitor", Critical Care Medicine, 17(9):929-933 (Sep. 1989).

International Search Report and Written Opinion issued in PCT/IB2012/051177, dated Jul. 19, 2012, 11 pages.

International Search Report for European Application No. 08157932, dated Nov. 19, 2008, 4 pages.

Steinke et al., "Role of Light Scattering in Whole Blood Oximetry", IEEE Transactions on Biomedical Engineering, BME-33(3):294-301 (Mar. 1986).

Zdrojkowski et al., "Optical Transmission and Reflection by Blood", IEEE Transactions on Biomedical Engineering, BME-17(2):122-128 (Apr. 1970).

International Preliminary Report on Patentability issued in PCT/IB2012/051177, dated Oct. 17, 2013, 8 pages.

* cited by examiner

FIG. 17

| PROTOCOL | BOWL | INLET BLOOD ||| | | COLLECTED RBC ||||| OIL VOLUME RATIO: P_opt / NEW PROTOCOL | RBC RECOVERY (%) | OIL REMOVAL (%) | PROCEDURE TIME (min:sec) |
|---|---|---|---|---|---|---|---|---|---|---|---|---|---|---|
| | | OIL VOLUME (%) | HCT (%) | PROCESSED INLET BLOOD VOLUME (mL) | OIL VOLUME (mL) | OIL VOLUME (%) | HCT (%) | COLLECTED RBC VOLUME (mL) | OIL VOLUME (mL) | | | | |
| P_opt | 55 | 4% | 25 | 171 | 7 | 6.39% | 53 | 60 | 3.83 | 10.95 | 74.31% | 43.88% | 05:09 |
| P_opt | 125 | 4% | 25 | 274 | 10 | 4.83% | 53 | 117 | 5.67 | 22.67 | 90.66% | 42.75% | 05:55 |
| P_opt | 175 | 4% | 25 | 342 | 13 | 4.89% | 51 | 160 | 7.83 | 24.74 | 96.38% | 39.14% | 04:53 |
| P_opt | 225 | 4% | 25 | 525 | 20 | 2.38% | 55 | 231 | 5.50 | 22.00 | 96.80% | 72.50% | 05:15 |
| P_opt | H 225 | 4% | 25 | 562 | 22 | 3.57% | 53 | 229 | 8.17 | 32.67 | 83.85% | 63.33% | |
| NEW OPTIMIZED PROTOCOL | 55 | 4% | 25 | 168 | 7 | 0.55% | 48 | 64 | 0.35 | | 72.57% | 94.79% | 06:40 |
| NEW OPTIMIZED PROTOCOL | 125 | 4% | 25 | 285 | 11 | 0.20% | 53 | 123 | 0.25 | | 91.93% | 97.64% | 06:57 |
| NEW OPTIMIZED PROTOCOL | 175 | 4% | 25 | 328 | 12 | 0.20% | 51 | 155 | 0.32 | | 95.66% | 97.44% | 06:24 |
| NEW OPTIMIZED PROTOCOL | 225 | 4% | 25 | 512 | 20 | 0.11% | 52 | 234 | 0.25 | | 94.86% | 98.73% | 07:55 |

SYSTEM FOR REMOVING UNDESIRABLE ELEMENTS FROM BLOOD USING A FIRST WASH STEP AND A SECOND WASH STEP

TECHNICAL FIELD

This disclosure relates to removing undesirable elements from blood in an autotransfusion system and in particular to a method and system for removing fat from the blood in an autotransfusion system.

BACKGROUND

In some medical procedures, such as intraoperative autotransfusion, blood lost by a patient is collected or salvaged to make it available for reinfusion back to the patient. Prior to reinfusion, the collected blood is cleaned to make it safer for the patient. Typically, red blood cells are separated from plasma that contains undesirable elements, such as fat, activated clotting proteins, anticoagulant, activated platelets, coagulation by-products, cellular debris, and free hemoglobin (Hgb). The red blood cells are reinfused back to the patient.

In some autotransfusion systems, the components of the blood are separated using a centrifuge bowl. Salvaged blood is put into the centrifuge bowl through an inlet tube and rotation of the centrifuge bowl causes the red blood cells, which are the heaviest cellular components of blood, to be propelled outward, compacting the red blood cells against the wall of the centrifuge bowl. Other cellular components, such as white blood cells and platelets, are arranged in a thin layer, referred to as a buffy coat, directly adjacent the concentrated mass of red blood cells. The plasma, which contains the undesirable elements, is situated in a layer nearer the axis of rotation than the buffy coat. As filling continues, more of the heavier components, i.e. the red blood cells, are pushed inwards, nearer to the axis of rotation, which pushes the lighter plasma, such as fat, out of an outlet at the top of the centrifuge bowl. The introduction of salvaged blood into the centrifuge bowl ceases once the centrifuge bowl has substantially filled with red blood cells.

Next, a washing solution, such as a saline solution, is pumped into the centrifuge bowl to wash the blood. Often, the washing solution is added at a steady flow rate to gradually take the place of the plasma and other unwanted elements that are expelled through the outlet from the centrifuge bowl. After washing, the centrifuge bowl contains concentrated red blood cells and washing solution, which can be collected in a reinfusion pouch or bag and made available for reinfusion back to the patient.

Manufacturers continuously strive to provide increased hematocrit (HCT) levels and decreased levels of the undesirable elements in the collected blood for reinfusion back to the patient.

SUMMARY

Example 1 is a system for removing undesirable elements from blood. The system includes a centrifuge bowl, a pump, and a controller. The centrifuge bowl to separate the blood into components according to relative densities of the components. The pump to provide wash solution that washes the blood in the centrifuge bowl. The controller operatively connected to the centrifuge bowl and the pump to wash the blood in the centrifuge bowl in a first wash and remove first undesirable elements and to wash the blood in the centrifuge bowl in a second wash and remove trapped undesirable elements. The controller to further mix the blood and the wash solution in the centrifuge bowl and provide diluted blood, separate the diluted blood into concentrated blood and the wash solution, fill the centrifuge bowl with previously concentrated blood to build a buffy coat, and empty the centrifuge bowl of the concentrated blood and the previously concentrated blood after the buffy coat is reached.

In Example 2, the system of Example 1 in which the controller is operatively connected to the centrifuge bowl and the pump to fill the centrifuge bowl with the blood and separate the blood into the components according to the relative densities of the components prior to the first wash.

In Example 3, the system of any of Examples 1 and 2 in which the controller is operatively connected to the centrifuge bowl and the pump to remove second undesirable elements prior to the first wash.

In Example 4, the system of any of Examples 1-3 in which the centrifuge bowl includes a collector that traps the trapped undesirable elements under the collector prior to the first wash.

In Example 5, the system of any of Examples 1-4 in which the controller is operatively connected to the centrifuge bowl and the pump to provide a first wash speed in the first wash and a second wash speed in the second wash, such that the second wash speed is greater than the first wash speed to remove the trapped undesirable elements from the centrifuge bowl.

In Example 6, the system of any of Examples 1-5 in which the centrifuge bowl includes a central tube such that the wash solution in the second wash flows through the central tube to remove the trapped undesirable elements from the centrifuge bowl.

In Example 7, the system of any of Examples 1-6 in which the controller is operatively connected to the centrifuge bowl and the pump to stop at least one of the centrifuge bowl from spinning and the pump to mix the blood and the wash solution in the centrifuge bowl and provide the diluted blood.

In Example 8, the system of any of Examples 1-7 in which the controller is operatively connected to the centrifuge bowl and the pump to remove a portion of the diluted blood from the centrifuge bowl and restore air balance prior to separating the diluted blood.

In Example 9, the system of any of Examples 1-8 in which one of the trapped undesirable elements is fat.

Example 10 is a system for removing undesirable elements from blood. The system includes a centrifuge bowl, a pump, and a controller. The centrifuge bowl to separate the blood into components according to relative densities of the components. The pump to provide wash solution that washes the blood in the centrifuge bowl. The controller operatively connected to the centrifuge bowl and the pump to wash the blood in the centrifuge bowl in a first wash at a first wash speed to remove first undesirable components and in a second wash at a second wash speed that is greater than the first wash speed to remove trapped undesirable elements from the centrifuge bowl. The controller to further mix the blood and the wash solution in the centrifuge bowl to provide diluted blood.

In Example 11, the system of Example 10 in which the controller is operatively connected to the centrifuge bowl and the pump to stop at least one of the centrifuge bowl from spinning and the pump to mix the blood and the wash solution in the centrifuge bowl to provide the diluted blood.

In Example 12, the system of any of Examples 10 and 11 in which the controller is operatively connected to the centrifuge bowl and the pump to remove a portion of the diluted blood from the centrifuge bowl and separate the diluted blood in the centrifuge bowl into concentrated blood and the wash solution.

In Example 13, the system of any of Examples 10-12 in which the controller is operatively connected to the centrifuge bowl and the pump to fill the centrifuge bowl with previously concentrated blood to build a buffy coat and empty the centrifuge bowl of the concentrated blood and the previously concentrated blood after reaching the buffy coat.

In Example 14, the system of any of Examples 10-13 in which the centrifuge bowl includes a collector that traps the trapped undesirable elements under the collector prior to the first wash and the centrifuge bowl includes a central tube and the wash solution in the second wash flows through the central tube to remove the trapped undesirable elements from under the collector.

Example 15 is a method for removing undesirable elements from blood. The method includes separating the blood into components according to relative densities of the components using a centrifuge bowl and removing first undesirable elements from the centrifuge bowl prior to a first wash. In the wash phase, the method includes washing the blood with wash solution in the first wash to remove second undesirable components from the centrifuge bowl and washing the blood with more of the wash solution in a second wash to remove trapped undesirable elements from the centrifuge bowl. The method further includes mixing the blood and the wash solution to provide diluted blood in the centrifuge bowl, removing some of the diluted blood from the centrifuge bowl, separating the diluted blood in the centrifuge bowl into concentrated blood and the wash solution, filling the centrifuge bowl with previously concentrated blood to build a buffy coat, and emptying the centrifuge bowl of the concentrated blood and the previously concentrated blood after reaching the buffy coat.

In Example 16, the method of Example 15 in which removing first undesirable elements includes trapping the trapped undesirable elements under a collector in the centrifuge bowl.

In Example 17, the method of any of Examples 15 and 16 in which washing the blood with wash solution in the first wash includes washing at a first wash speed and washing the blood with more of the wash solution in a second wash includes washing at a second wash speed that is greater than the first wash speed.

In Example 18, the method of any of Examples 15-17 in which washing the blood with more of the wash solution in a second wash includes pumping the wash solution through a central tube in the centrifuge bowl.

In Example 19, the method of any of Examples 15-18 in which mixing the blood and the wash solution includes stopping at least one of the centrifuge bowl from spinning and a pump.

Example 20 is a method for removing undesirable elements from blood. The method includes separating the blood into components according to relative densities of the components using a centrifuge bowl and removing first undesirable elements from the centrifuge bowl. In a wash phase, the method includes washing the blood with wash solution in a first wash at a first wash speed to remove second undesirable components from the centrifuge bowl and washing the blood with more of the wash solution in a second wash at a second wash speed that is greater than the first wash speed to remove trapped undesirable elements from the centrifuge bowl. The method further includes mixing the blood and the wash solution to provide diluted blood in the centrifuge bowl.

In Example 21, the method of Example 20 in which mixing the blood and the wash solution to provide diluted blood in the centrifuge bowl comprises stopping at least one of the centrifuge bowl from spinning and a pump.

In Example 22, the method of any of Examples 20 and 21 including removing some of the diluted blood from the centrifuge bowl and separating the diluted blood left in the centrifuge bowl into concentrated blood and the wash solution.

In Example 23, the method of any of Examples 20-22 including filling the centrifuge bowl with previously concentrated blood to build a buffy coat and emptying the centrifuge bowl of the concentrated blood and the previously concentrated blood after reaching the buffy coat.

In Example 24, the method of any of Examples 20-23 in which removing first undesirable elements includes trapping the trapped undesirable elements under a collector in the centrifuge bowl and washing the blood with more of the wash solution in a second wash includes pumping the wash solution through a central tube in the centrifuge bowl.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 17 is a table illustrating test results, according to some embodiments described in the disclosure.

Figure 1:
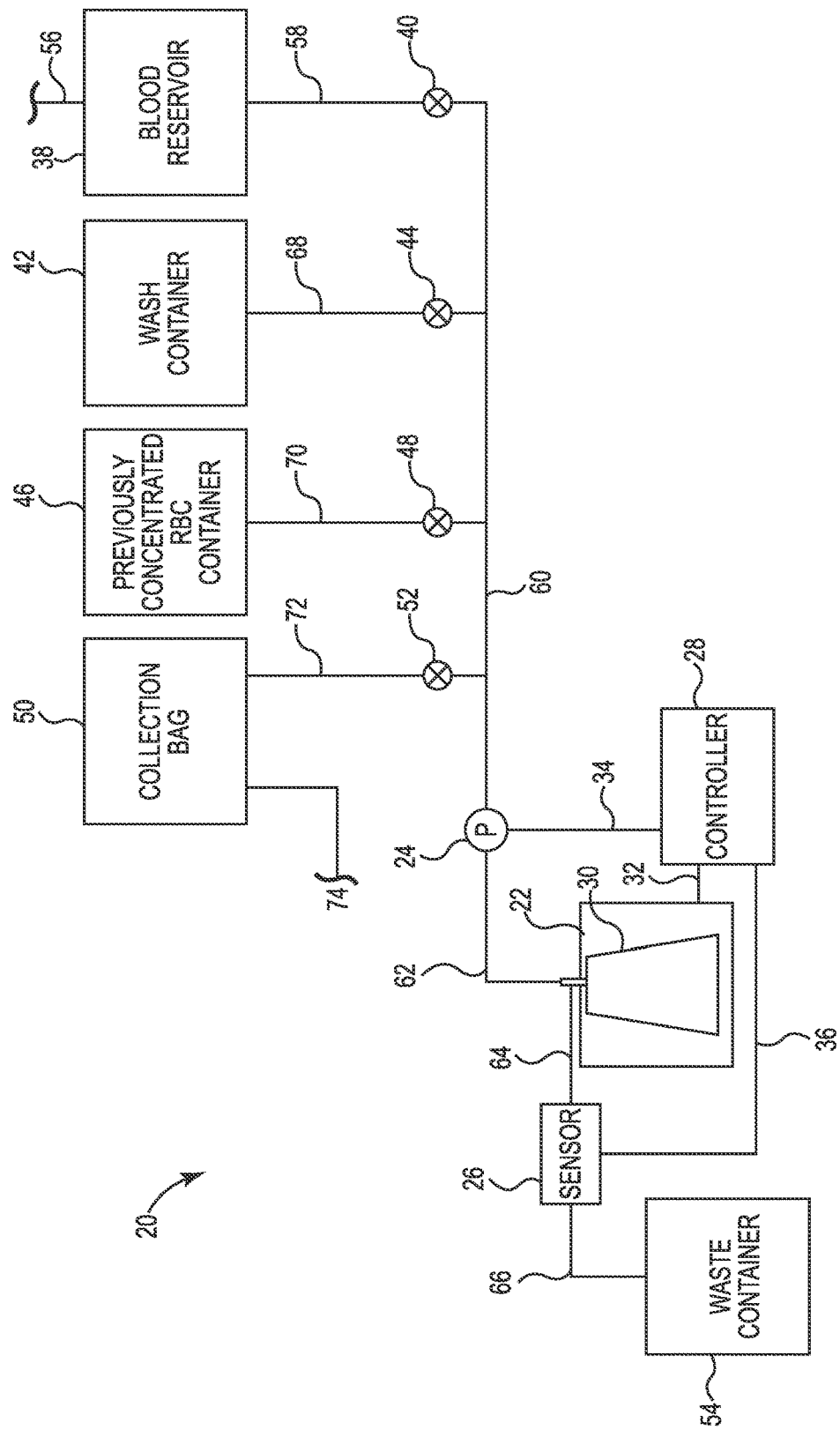
FIG. 1 is a diagram illustrating an autotransfusion system, according to some embodiments described in the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a diagram illustrating an autotransfusion system 20, according to some embodiments described in the disclosure. The autotransfusion system 20 includes a centrifuge 22, a pump 24, a sensor 26, and a controller 28. A centrifuge bowl 30 is situated in the centrifuge 22. The controller 28 is operatively connected to the centrifuge 22 including the centrifuge bowl 30, the pump 24, and the sensor 26 to provide the autotransfusion system 20. The controller 28 is communicatively coupled to the centrifuge 22 through a first communications path 32, to the pump 24 through a second communications path 34, and to the sensor 26 through a third communications path 36.

In some embodiments, the autotransfusion system 20 further includes a salvaged blood reservoir 38 and a salvaged blood valve 40, a wash solution container 42 and a wash solution valve 44, a previously concentrated red blood cell container 46 and a red blood cell valve 48, a collection bag 50 and a collection valve 52, and a waste container 54. Optionally, in some embodiments, the previously concentrated red blood cell container 46 and the red blood cell valve 48 are not included in the autotransfusion system 20, and the collection bag 50 and the collection valve 52 provide the services of the previously concentrated red blood cell container 46 and the red blood cell valve 48.

In some embodiments, the controller 28 is operatively connected to each of the salvaged blood valve 40, the wash solution valve 44, the red blood cell valve 48, and the collection valve 52 to control them in the autotransfusion system 20. In some embodiments, the controller 28 is communicatively coupled (not shown for clarity) to each of the salvaged blood valve 40, the wash solution valve 44, the red blood cell valve 48, and the collection valve 52.

In the autotransfusion system 20, an inlet line 56 suctions salvaged blood from the operative field or from another blood source (not shown) and carries the suctioned blood to the salvaged blood reservoir 38. In a fill phase, the salvaged blood in the salvaged blood reservoir 38 is pumped through a salvaged blood line 58 and the salvaged blood valve 40 into a system line 60 by the pump 24. The salvaged blood is further pumped through a bowl inlet line 62 and into the centrifuge bowl 30 by the pump 24. As the salvaged blood is pumped into the centrifuge bowl 30, the salvaged blood valve 40 is open and the other valves, including the wash solution valve 44, the red blood cell valve 48, and the collection valve 52, are closed. In some embodiments, the centrifuge bowl 30 receives the shed or salvaged blood directly from the operative field or directly from the other source.

In the fill phase, the centrifuge bowl 30 is filled with the salvaged blood as the centrifuge bowl 30 rotates or spins in the centrifuge 22. The spinning centrifuge bowl 30 separates the blood into components according to the relative densities of the components. The red blood cells, which are the densest components of the blood, are propelled outward, against the circumferential wall of the centrifuge bowl 30. Other components, such as white blood cells and platelets, are arranged in a thin layer, referred to as the buffy coat, directly adjacent the concentrated mass of red blood cells. The plasma layer is situated nearer the axis of rotation than the buffy coat, with a fat layer being the least dense component situated in the area nearest to the axis of rotation. As filling the centrifuge bowl 30 continues, more of the red blood cells are pushed inwards, nearer to the axis of rotation, which pushes the fat out of an outlet at the top of the centrifuge bowl 30. The fat flows through a first waste line 64 connected to the outlet of the centrifuge bowl 30, past the sensor 26, and through a second waste line 66 into the waste container 54. The sensor 26 senses when the buffy coat begins to come out of the outlet or when the buffy coat is at or near the top of the centrifuge bowl 30 and the sensor 26 provides a corresponding signal to the controller 28. In response to the signal from the sensor 26, the controller 28 stops the fill phase, which traps some of the fat in the centrifuge bowl 30. The autotransfusion system 20 provides further steps to remove the trapped fat and reduce the amount of fat in the finished product.

After the fill phase, the autotransfusion system 20 washes the blood in the centrifuge bowl 30 in a two part wash phase. Wash solution contained in the wash solution container 42 is pumped into the centrifuge bowl 30 by the pump 24. The wash solution is pumped through a wash solution line 68 and the wash solution valve 44 into the system line 60 by the pump 24. The wash solution is further pumped through the bowl inlet line 62 and into the centrifuge bowl 30 by the pump 24. As the wash solution is pumped into the centrifuge bowl 30, the wash solution valve 44 is open and the other valves, including the salvaged blood valve 40, the red blood cell valve 48, and the collection valve 52, are closed. In some embodiments, the wash solution is a saline solution.

In a first wash of the wash phase, the controller 28 controls the centrifuge bowl 30 and the pump 24 to wash the blood in the centrifuge bowl 30 at a slower first wash speed. The first wash removes more of the plasma or supernatant that includes the undesirable components, such as fat, activated clotting proteins, anticoagulant, activated platelets, coagulation by-products, cellular debris, and free Hgb.

In a second wash of the wash phase, the controller 28 controls the centrifuge bowl 30 and the pump 24 to wash the blood in the centrifuge bowl 30 at a faster second wash speed. The second wash at the faster wash speed removes the fat that was trapped in the centrifuge bowl 30 during the fill phase. After the second wash, the wash solution from the second wash remains in the centrifuge bowl 30, such that the collected red blood cells would be diluted by the wash solution and provide a lower HCT value. The autotransfusion system 20 provides further steps to remove the wash solution and provide a higher HCT value in the finished product, which also has reduced fat content.

In some embodiments, the slower first wash speed and the faster second wash speed are provided by changing one or more of the flow rate of the wash solution and the rotational speed of the centrifuge bowl 30.

After the two part wash phase, the controller 28 controls the centrifuge bowl 30 and the pump 24 to mix the concentrated red blood cells and the wash solution in the centrifuge bowl 30 and provide a diluted red blood cell mixture having a lower HCT value. In some embodiments, the controller 28 stops the centrifuge bowl 30 from spinning and the pump 24 to mix the concentrated red blood cells and the wash solution to provide the diluted red blood cell mixture.

After mixing the concentrated red blood cells and the wash solution, a small quantity of the diluted red blood cell mixture is drawn off to restore air balance in the centrifuge bowl 30. Then, the controller 28 restarts the centrifuge 22 to spin the centrifuge bowl 30 and separate the diluted red blood cell mixture into concentrated red blood cells and the wash solution. In some embodiments, about 50 milliliters of the diluted red blood cell mixture is drawn off. In some embodiments, some of the diluted red blood cell mixture is drawn off by the pump 24 and discarded in a diluted red blood cell container (not shown).

To rebuild the buffy coat, previously concentrated red blood cells in the previously concentrated red blood cell container 46 are pumped into the centrifuge bowl 30 by the pump 24. The previously concentrated red blood cells are pumped through a red blood cell line 70 and the red blood cell valve 48 into the system line 60 by the pump 24. The previously concentrated red blood cells are further pumped through the bowl inlet line 62 and into the centrifuge bowl 30 by the pump 24. As the previously concentrated red blood cells are pumped into the centrifuge bowl 30, the red blood cell valve 48 is open and the other valves, including the salvaged blood valve 40, wash solution valve 44, and the collection valve 52, are closed.

Optionally, in some embodiments, the previously concentrated red blood cell container 46 and the red blood cell valve 48 are not included in the autotransfusion system 20 and the previously concentrated red blood cells are pumped from the collection bag 50 through a collection line 72 and the collection valve 52 into the system line 60 by the pump 24. The previously concentrated red blood cells are further pumped through the bowl inlet line 62 and into the centrifuge bowl 30 by the pump 24. As the previously concentrated red blood cells are pumped into the centrifuge bowl 30 from the collection bag 50, the collection valve 52 is open and the other valves, including the salvaged blood valve 40 and the wash solution valve 44, are closed.

The sensor 26 senses when the buffy coat begins to come out of the outlet or when the buffy coat is at or near the top of the centrifuge bowl 30 and the sensor 26 provides a corresponding signal to the controller 28. In response to the signal from the sensor 26, the controller 28 stops refilling the centrifuge bowl 30 with the previously concentrated red blood cells and proceeds to the emptying phase.

In the emptying phase, the final product is pumped out of the centrifuge bowl 30 through the bowl inlet line 62 and into the system line 60 by the pump 24. The final product is further pumped through the collection valve 52 and the collection line 72 into the collection bag 50. In the emptying phase, the controller 28 opens the collection valve 52 and closes all other valves, including the salvaged blood valve 40, wash solution valve 44, and the red blood cell valve 48.

The final product in the collection bag 50 can be used for reinfusion back to the patient via outlet line 74. The final product includes concentrated red blood cells with a higher HCT value and a lower concentration of fat than otherwise obtained.

Figure 2:
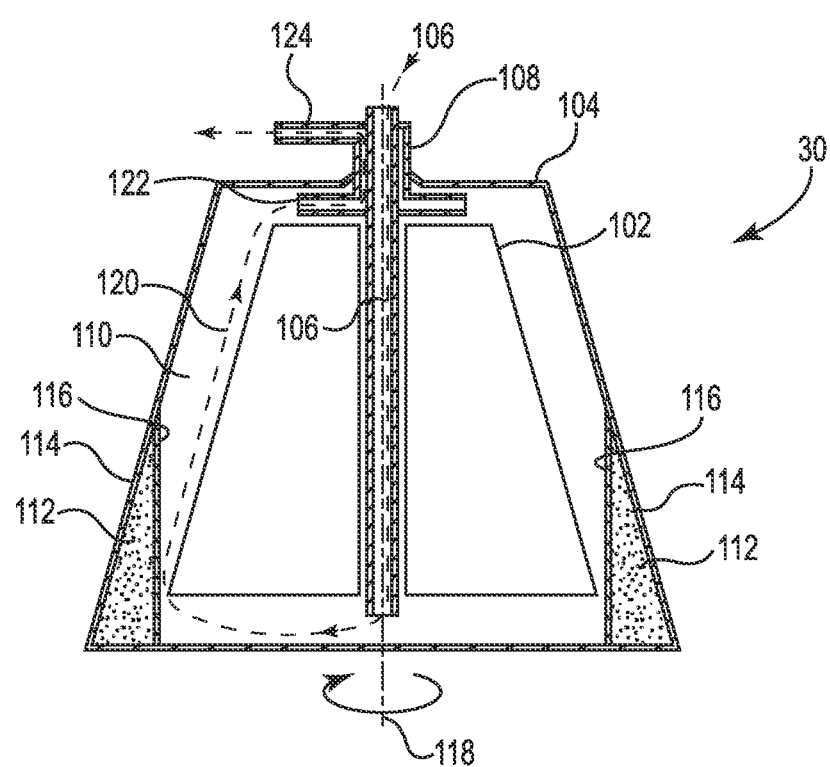
FIG. 2 is a diagram illustrating the centrifuge bowl, according to some embodiments described in the disclosure.

FIG. 2 is a diagram illustrating the centrifuge bowl 30, according to some embodiments described in the disclosure. The centrifuge bowl 30 includes an inner bell 102 and an outer bell 104 that are rigidly coupled together and made to rotate in the centrifuge 22. Blood entering the centrifuge bowl 30 follows path 106 through an inlet tube or chamber 108 and into a separation chamber 110 situated between the inner bell 102 and the outer bell 104. The rotation of the centrifuge bowl 30 creates a centrifugal force that causes the blood within the separation chamber 110 to separate into different fractions based on the density of the blood components. The centrifugal force causes red blood cells 112, which are higher density components of blood, to be propelled outward, against the circumferential wall 114 of the centrifuge bowl 30. Intermediate density blood components, such as white blood cells and platelets, are arranged in the thin layer known as the buffy coat 116, directly adjacent the concentrated mass of red blood cells 112. Lower density components, such as plasma that contains undesirable elements such as fat, are arranged in a layer (not shown in FIG. 2) that lies nearer the axis of rotation than the buffy coat 116.

As the centrifuge bowl 30 is filled, the higher density components push the lighter density blood components inwards, closer to a rotational axis 118 of the centrifuge bowl 30. Eventually, the lighter density components, such as the fat, are displaced out of the centrifuge bowl 30 following path 120 through a collector 122 and an outlet chamber 124. The lighter density components flow through first and second waste lines 64 and 66 and into the waste container 54. Once the centrifuge bowl 30 has substantially filled with red blood cells 112 as indicated by a sensing mechanism, such as sensor 26 or a sensor located within the space between the inner bell 102 and the outer bell 104, the introduction of blood into the centrifuge bowl 30 ceases. The process continues as described in this disclosure.

Figure 3:
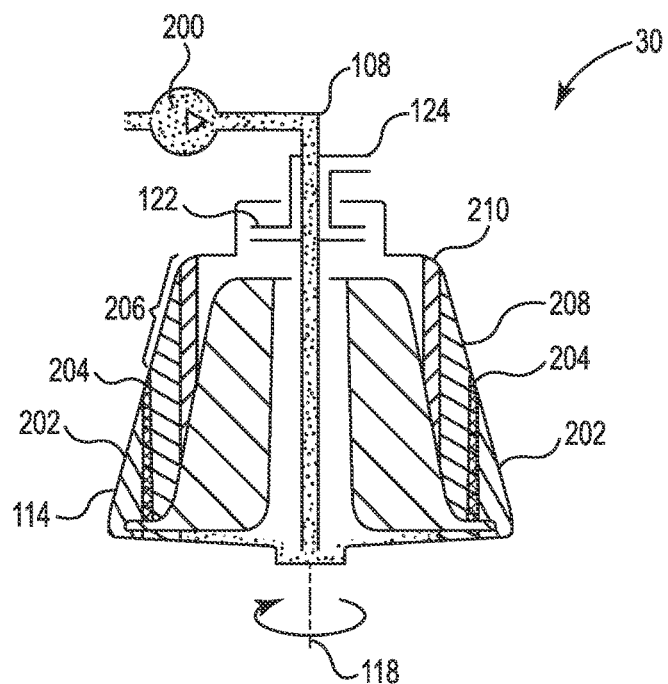
FIG. 3 is a diagram illustrating the centrifuge bowl receiving the salvaged blood in the fill phase, according to some embodiments described in the disclosure.
Figure 4:
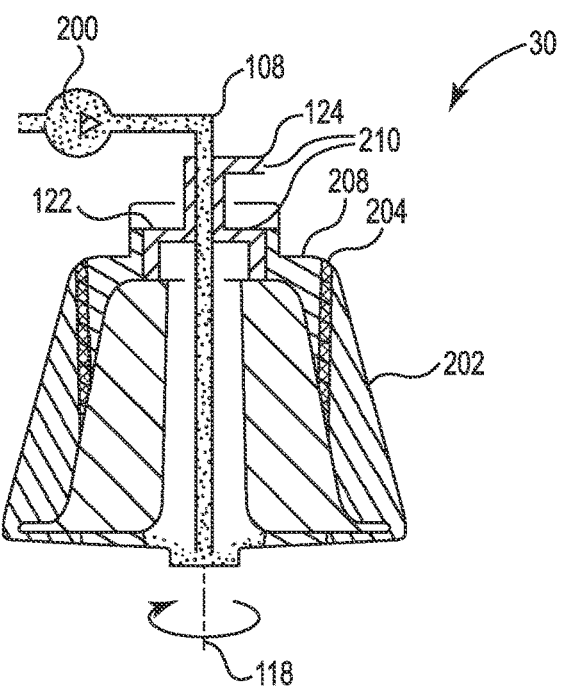
FIG. 4 is a diagram illustrating the centrifuge bowl being filled with the salvaged blood and some of the fat layer being expelled from the centrifuge bowl, according to some embodiments described in the disclosure.
Figure 5:
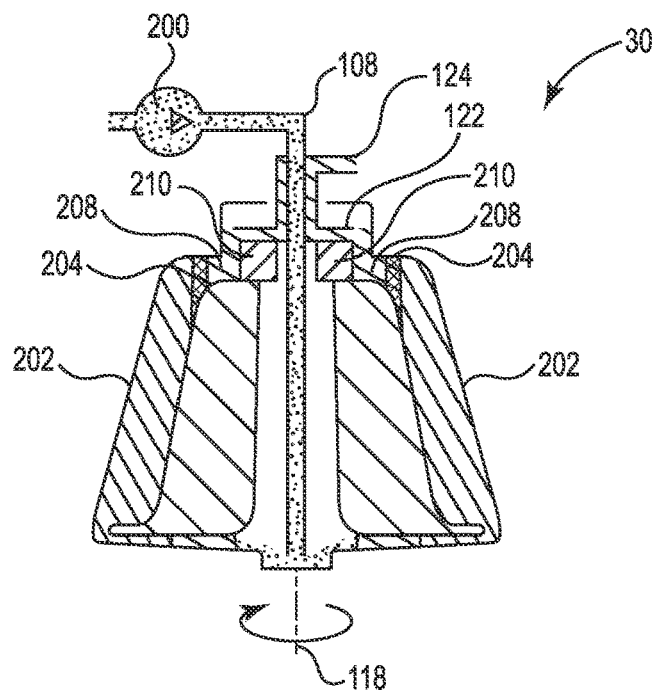
FIG. 5 is a diagram illustrating some of the supernatant layer being expelled from the centrifuge bowl and the trapped portion of the fat layer under the collector during the fill phase, according to some embodiments described in the disclosure.

FIGS. 3-5 are diagrams illustrating the fill phase of the autotransfusion system 20, according to some embodiments described in the disclosure. In some embodiments, the inlet line 56 suctions salvaged blood 200 from the operative field or from another blood source and carries the suctioned blood 200 to the salvaged blood reservoir 38. In some embodiments, the inlet line 56 suctions the salvaged blood 200 from the operative field or from another blood source and carries it directly to the inlet tube 108 of the centrifuge bowl 30.

FIG. 3 is a diagram illustrating the centrifuge bowl 30 receiving the salvaged blood 200 in the fill phase, according to some embodiments described in the disclosure. The centrifuge bowl 30 receives the salvaged blood 200 through the inlet tube 108 as the centrifuge bowl 30 rotates or spins in the centrifuge 22. The spinning centrifuge bowl 30 separates the salvaged blood 200 into components according to the relative densities of the components. The red blood cells 202, which are the densest components of the blood, are propelled outward, against the circumferential wall 114 of the centrifuge bowl 30. The buffy coat 204 that contains other components, such as white blood cells and platelets, is arranged in a thin layer directly adjacent the concentrated mass of red blood cells 202. The plasma layer 206 is situated nearer the axis of rotation than the buffy coat 204 and includes a supernatant layer 208 that contains little fat and a fat layer 210 that is the least dense component of the salvaged blood 200 and situated in the plasma layer 206 nearest to the axis of rotation adjacent the supernatant layer 208.

FIG. 4 is a diagram illustrating the centrifuge bowl 30 being filled with the salvaged blood 200 and some of the fat layer 210 being expelled from the centrifuge bowl 30, according to some embodiments described in the disclosure. As the fill phase continues, more of the red blood cells 202 are pushed inward, nearer to the axis of rotation. This pushes some of the fat layer 210 out of the collector 122 and the outlet chamber 124 at the top of the centrifuge bowl 30 and it pushes some of the fat layer 210 under the collector 122. The expelled portion of the fat layer 210 flows through the first waste line 64 connected to the outlet chamber 124, past the sensor 26, and through the second waste line 66 into the waste container 54. The portion of the fat layer 210 under the collector 122 remains trapped under the collector 122.

FIG. 5 is a diagram illustrating some of the supernatant layer 208 being expelled from the centrifuge bowl 30 and the trapped portion of the fat layer 210 under the collector 122 during the fill phase, according to some embodiments described in the disclosure. As the fill phase further continues, more of the red blood cells 202 are pushed inward, nearer to the axis of rotation, and some of the supernatant layer 208 is pushed out of the collector 122 and the outlet chamber 124 at the top of the centrifuge bowl 30. The expelled portion of the supernatant layer 208 flows through the first waste line 64 connected to the outlet chamber 124, past the sensor 26, and through the second waste line 66 into the waste container 54. The trapped portion of the fat layer 210 increases in size to substantially fill the area under the collector 122.

The sensor 26 senses when the buffy coat 204 begins to come out of the outlet chamber 124 or when the buffy coat 204 is at or near the top of the centrifuge bowl 30 and the sensor 26 provides a corresponding signal to the controller 28. In response to the signal from the sensor 26, the controller 28 stops the fill phase and the trapped portion of the fat layer 210 remains trapped under the collector 122. The autotransfusion system 20 provides further steps to remove the trapped portion of the fat layer 210 and reduce the amount of fat in the finished product.

Figure 6:
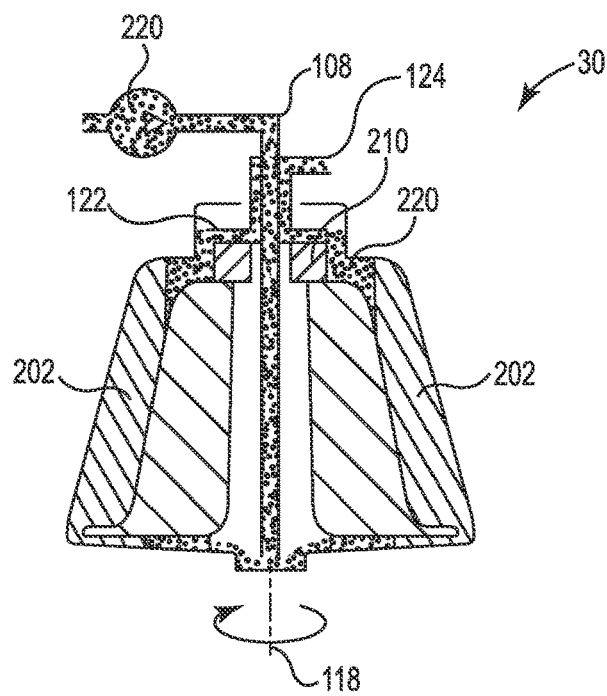
FIG. 6 is a diagram illustrating the first wash of the two part wash phase, according to some embodiments described in the disclosure.
Figure 7:
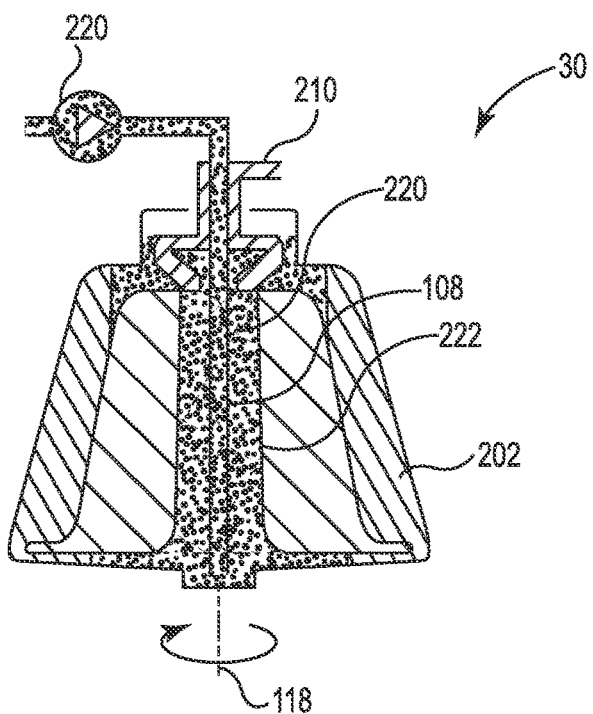
FIG. 7 is a diagram illustrating the second wash of the two part wash phase, according to some embodiments described in the disclosure.
Figure 8:
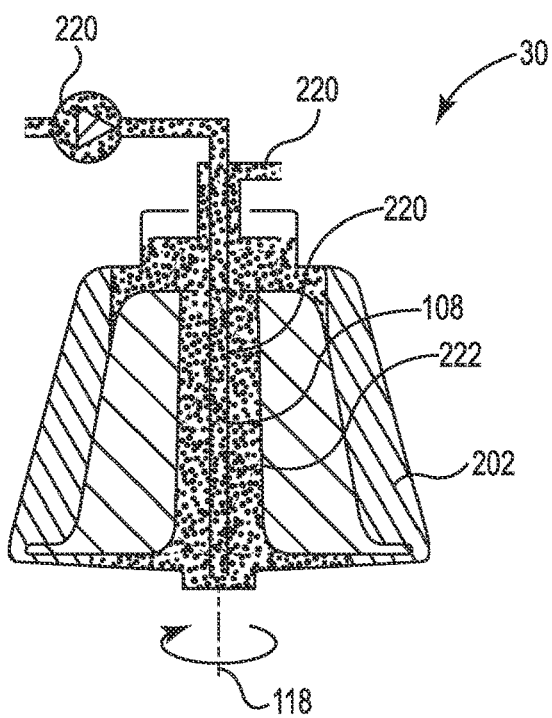
FIG. 8 is a diagram illustrating the centrifuge bowl toward the end of the second wash, according to some embodiments described in the disclosure.

FIGS. 6-8 are diagrams illustrating the two part wash phase of the autotransfusion system 20, according to some embodiments described in the disclosure. After the fill phase, the autotransfusion system 20 washes the red blood cells 202 in the centrifuge bowl 30 with a wash solution 220 in the two part wash phase. The wash solution 220 contained in the wash solution container 42 is pumped into the spinning centrifuge bowl 30 through the inlet tube 108 by the pump 24. In some embodiments, the wash solution 220 is a saline solution.

FIG. 6 is a diagram illustrating the first wash of the two part wash phase, according to some embodiments described in the disclosure. The controller 28 controls the centrifuge bowl 30 and the pump 24 to wash the red blood cells 202 in the centrifuge bowl 30 in the first wash at a slower first wash speed. The controller 28 spins the centrifuge bowl 30 and controls the pump 24 to pump the wash solution 220 into the centrifuge bowl 30 through the inlet tube 108. In some embodiments, the slower first wash speed is achieved by adjusting one or more of the flow rate of the wash solution 220 and the rotational speed of the centrifuge bowl 30.

In the first wash, the wash solution 220 enters the centrifuge bowl 30 through the inlet tube 108 and flows into the separation chamber 110, where it is separated from the red blood cells 202. As the first wash continues, the wash solution 220 is pushed inwards, nearer to the axis of rotation, and the less dense supernatant layer 208 is pushed out of the collector 122 and the outlet chamber 124 at the top of the centrifuge bowl 30. The expelled supernatant layer 208 flows through the first waste line 64 connected to the outlet chamber 124, past the sensor 26, and through the second waste line 66 into the waste container 54. The first wash removes more of the supernatant layer 208. The trapped portion of the fat layer 210 under the collector 122 remains substantially unaffected by the wash solution 220 in the first wash.

FIG. 7 is a diagram illustrating the second wash of the two part wash phase, according to some embodiments described in the disclosure. The controller 28 controls the centrifuge bowl 30 and the pump 24 to wash the red blood cells 202 in the centrifuge bowl 30 in the second wash at a second wash speed that is faster than the slower first wash speed. The controller 28 spins the centrifuge bowl 30 and controls the pump 24 to pump the wash solution 220 into the centrifuge bowl 30 through the inlet tube 108. The wash solution 220 is forced down through the inlet tube 108 and up through a central tube 222 of the centrifuge bowl 30.

The central tube 222 extends from the top of the inner bell 102 to the bottom of the centrifuge 30 and is situated around the inlet tube 108, such that the inlet tube 108 extends from the top of the centrifuge bowl 30 toward the bottom of the centrifuge bowl 30 through the central tube 222. At the top of the centrifuge bowl 30, the central tube 222 is in fluidic contact with the underside of the collector 122 and the trapped portion of the fat layer 210. The second wash removes the trapped portion of the fat layer 210 from under the collector 122, where the wash solution 220 pushes the trapped portion of the fat layer 210 out of the collector 122 and the outlet chamber 124 at the top of the centrifuge bowl 30. The expelled portion of the fat layer 210 flows through the first waste line 64 connected to the outlet chamber 124, past the sensor 26, and through the second waste line 66 into the waste container 54. In some embodiments, the faster second wash speed is achieved by adjusting one or more of the flow rate of the wash solution 220 and the rotational speed of the centrifuge bowl 30. In some embodiments, the slower first wash speed has a slower flow rate of the wash solution 220 and the faster second wash speed has a higher flow rate of the wash solution 220 in relation to the slower flow rate of the slower first wash speed.

FIG. 8 is a diagram illustrating the centrifuge bowl 30 toward the end of the second wash, according to some embodiments described in the disclosure. After the second wash, excess of wash solution 220 remains in the centrifuge bowl 30, including in the inlet tube 108 and the central tube 222. This excess of wash solution 220 would dilute the collected red blood cells 202 and provide a lower HCT value. The autotransfusion system 20 provides further steps to remove the excess of wash solution 220 and provide a higher HCT value in the finished product that also has reduced fat content.

Figure 9:
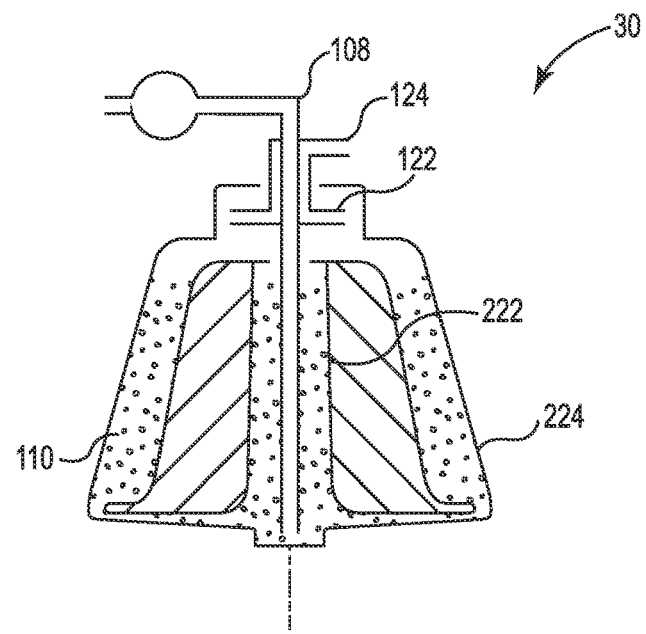
FIG. 9 is a diagram illustrating the centrifuge bowl with a diluted red blood cell mixture, according to some embodiments described in the disclosure.

FIG. 9 is a diagram illustrating the centrifuge bowl 30 filled with a diluted red blood cell mixture 224, according to some embodiments described in the disclosure. After the two part wash phase, the controller 28 controls the centrifuge bowl 30 and the pump 24 to mix the concentrated red blood cells 202 and the wash solution 220 in the centrifuge bowl 30 to provide the diluted red blood cell mixture 224. In the centrifuge bowl 30, the diluted red blood cell mixture 224 is in at least the separation chamber 110 and the central tube 222. The diluted red blood cell mixture 224 has a lower HCT value than the final product 228 (shown in FIG. 14). In some embodiments, the controller 28 stops the centrifuge bowl 30 from spinning to mix the concentrated red blood cells 202 and the wash solution 220 and provide the diluted red blood cell mixture 224. In some embodiments, the controller 28 stops the centrifuge bowl 30 from spinning and the controller 28 stops the pump 24 to mix the concentrated red blood cells 202 and the wash solution 220 and provide the diluted red blood cell mixture 224.

Figure 10:
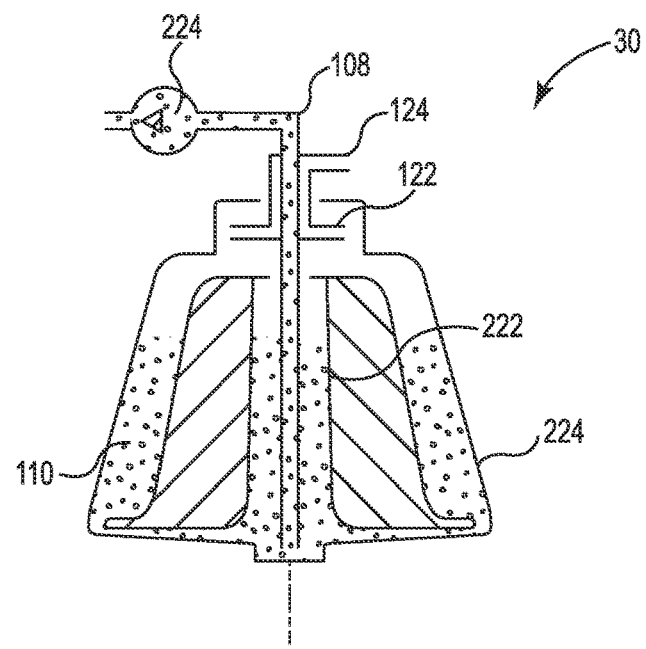
FIG. 10 is a diagram illustrating some of the diluted red blood cell mixture being removed from the centrifuge bowl, according to some embodiments described in the disclosure.

FIG. 10 is a diagram illustrating some of the diluted red blood cell mixture 224 being removed from the centrifuge bowl 30, according to some embodiments described in the disclosure. After mixing the concentrated red blood cells 202 and the wash solution 220, a small quantity of the diluted red blood cell mixture 224 is drawn off to restore air balance in the centrifuge bowl 30. In some embodiments, some of the diluted red blood cell mixture 224 is pumped out of the centrifuge bowl 30 through the inlet tube 108 by the pump 24. In some embodiments, the diluted red blood cell mixture 224 that is pumped out of the centrifuge bowl 30 is stored in a diluted red blood cell container (not shown). In some embodiments, about 50 milliliters of the diluted red blood cell mixture 224 is drawn off to restore air balance in the centrifuge bowl 30. In some embodiments, the centrifuge bowl 30 remains stopped to remove the small quantity of the diluted red blood cell mixture 224. In some embodiments, the controller 28 stops the centrifuge bowl 30 from spinning to remove the small quantity of the diluted red blood cell mixture 224.

Figure 11:
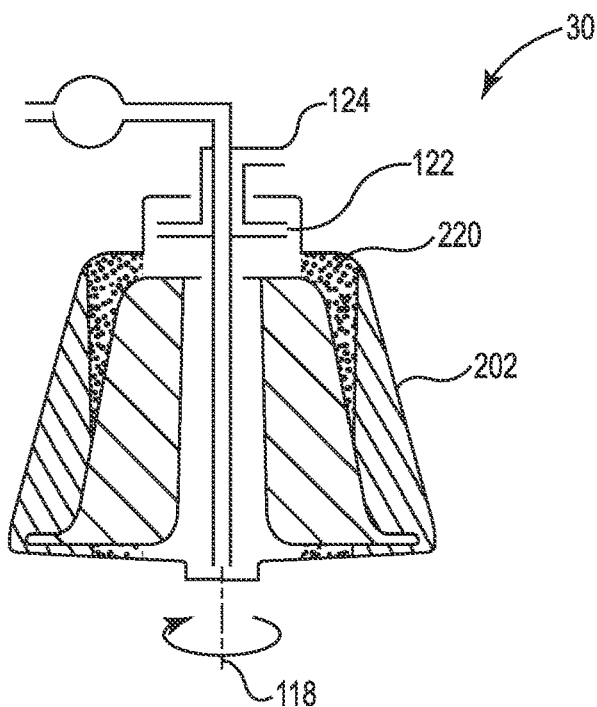
FIG. 11 is a diagram illustrating the centrifuge bowl as it spins after being restarted in the autotransfusion system, according to some embodiments described in the disclosure.

FIG. 11 is a diagram illustrating the centrifuge bowl 30 as it spins after being restarted in the autotransfusion system 20, according to some embodiments described in the disclosure. After some of the diluted red blood cell mixture 224 have been removed, the controller 28 restarts the centrifuge 22 to spin the centrifuge bowl 30 and separate the diluted red blood cell mixture 224 into concentrated red blood cells 202 and the wash solution 220.

Figure 12:
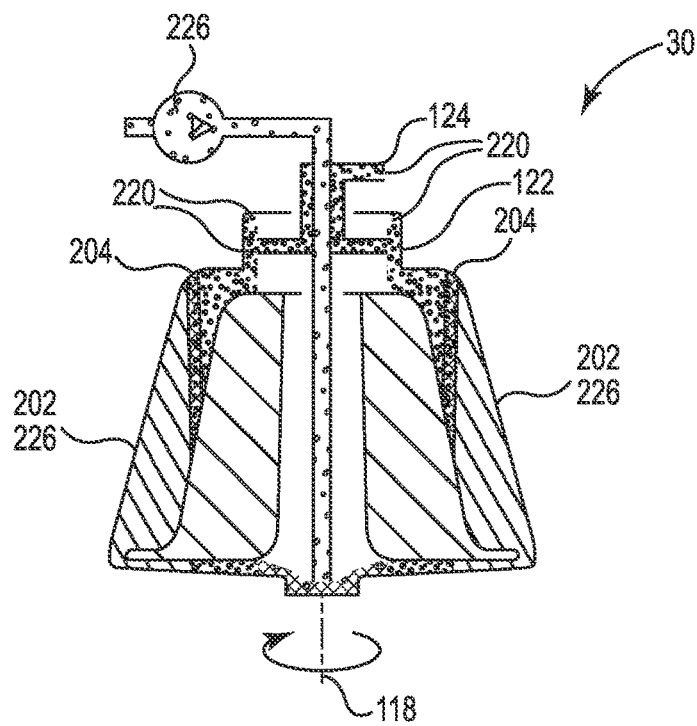
FIG. 12 is a diagram illustrating the previously concentrated red blood cells being pumped into the spinning centrifuge bowl, according to some embodiments described in the disclosure.
Figure 13:
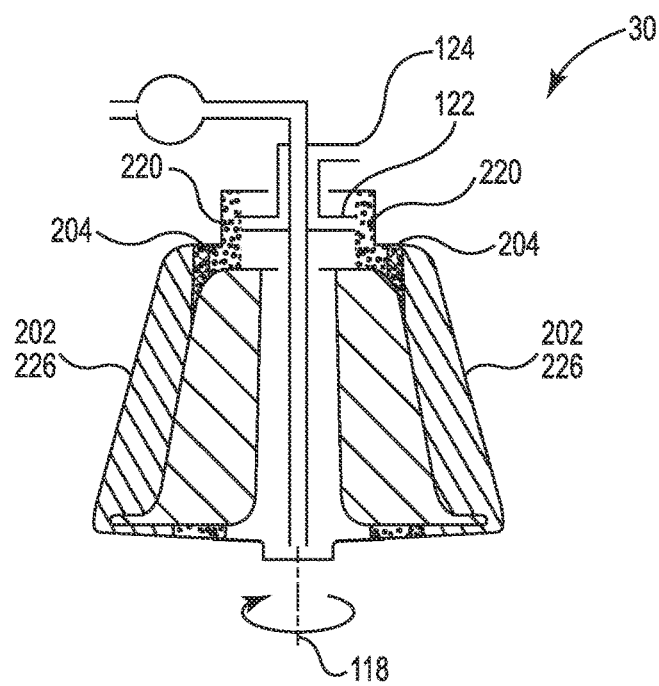
FIG. 13 is a diagram illustrating the centrifuge bowl after rebuilding the buffy coat, according to some embodiments described in the disclosure.

FIGS. 12 and 13 are diagrams illustrating the autotransfusion system 20 rebuilding the buffy coat 204 prior to emptying the final product 228 (shown in FIG. 14) from the centrifuge bowl 30, according to some embodiments described in the disclosure. To rebuild the buffy coat 204, previously concentrated red blood cells 226 are pumped into the centrifuge bowl 30 by the pump 24. In some embodiments, the previously concentrated red blood cells 226 are pumped from the previously concentrated red blood cell container 46 into the centrifuge bowl 30. Optionally, in some embodiments, the previously concentrated red blood cells 226 are pumped from the collection bag 50 into the centrifuge bowl 30.

FIG. 12 is a diagram illustrating the previously concentrated red blood cells 226 being pumped into the spinning centrifuge bowl 30, according to some embodiments described in the disclosure. As the previously concentrated red blood cells 226 are pumped into the centrifuge bowl 30, the centrifuge bowl 30 spins to separate the components into the red blood cells 202 and 226 and the wash solution 220. As more of the red blood cells 202 and 226 are pushed inwards, nearer to the axis of rotation, the wash solution 220 is pushed out of the collector 122 and the outlet chamber 124 at the top of the centrifuge bowl 30. The expelled portion of the wash solution 220 flows through the first waste line 64 connected to the outlet chamber 124, past the sensor 26, and through the second waste line 66 and into the waste container 54.

FIG. 13 is a diagram illustrating the centrifuge bowl 30 after rebuilding the buffy coat 204, according to some embodiments described in the disclosure. The sensor 26 senses when the buffy coat 204 begins to come out of the outlet or when the buffy coat 204 is at or near the top of the centrifuge bowl 30 and the sensor 26 provides a corresponding signal to the controller 28. In response to the signal from the sensor 26, the controller 28 stops refilling the centrifuge bowl 30 with the previously concentrated red blood cells 226. After rebuilding the buffy coat 204, the centrifuge bowl 30 includes the red blood cells 202 and 226, at least some of the buffy coat 204, and possibly some of the wash solution 220. The autotransfusion system 20 proceeds to the emptying phase.

Figure 14:
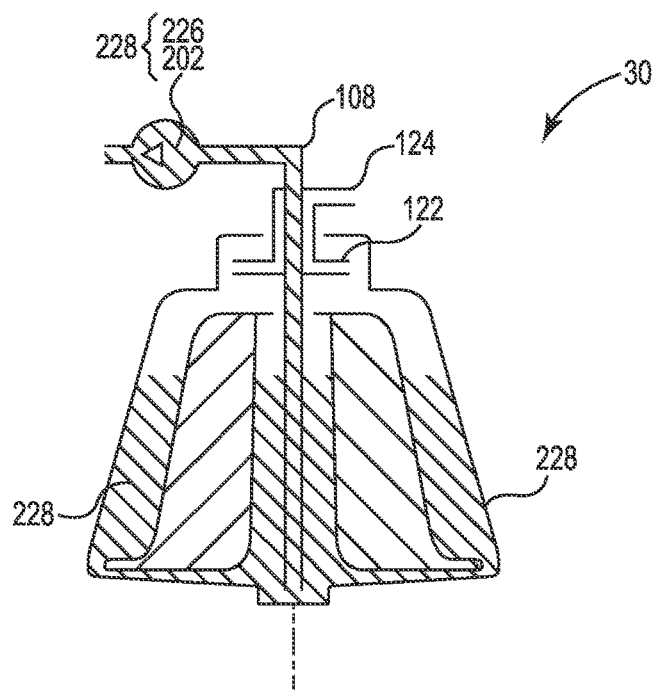
FIG. 14 is a diagram illustrating the emptying phase of the autotransfusion system 20, according to some embodiments described in the disclosure.

FIG. 14 is a diagram illustrating the emptying phase of the autotransfusion system 20, according to some embodiments described in the disclosure. In the emptying phase, the final product 228 that includes the concentrated red blood cells 202 and the previously concentrated red blood cells 226 pumped into the centrifuge bowl 30, is pumped out of the centrifuge bowl 30 through the inlet tube 108 and the collection valve 52 and into the collection bag 50. The centrifuge bowl 30 can be completely emptied only when the centrifuge 22 and the centrifuge bowl 30 come to a complete stop. The final product 228 in the collection bag 50 includes the concentrated red blood cells 202 and the previously concentrated red blood cells 226 pumped out of the centrifuge bowl 30. This final product 228 can be used for reinfusion back to the patient via outlet line 74. The autotransfusion system 20 provides a final product 228 that includes concentrated red blood cells 202 and 226 with a higher HCT value and a lower concentration of fat than obtained in some other systems. In some embodiments, the controller 28 and the centrifuge 22 continue spinning the centrifuge bowl 30 during at least part of the emptying phase. In some embodiments, the controller 28 stops the centrifuge 22 from spinning the centrifuge bowl 30 during all of the emptying phase.

Figure 15:
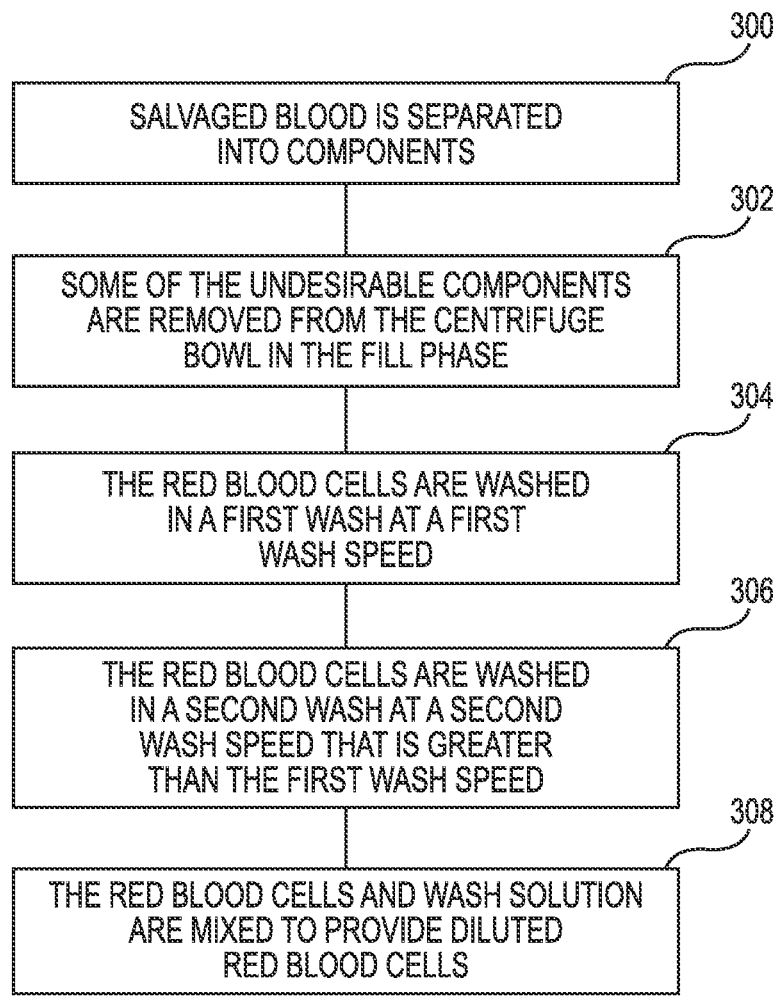
FIG. 15 is a flow chart diagram illustrating a method for removing undesirable elements from salvaged blood, according to some embodiments described in the disclosure.

FIG. 15 is a flow chart diagram illustrating a method for removing undesirable elements from the salvaged blood 200, according to some embodiments described in the disclosure.

At 300, the salvaged blood 200 is separated into components according to the relative densities of the components using the centrifuge bowl 30. The centrifuge bowl 30 is filled with the salvaged blood 200 as the centrifuge bowl 30 rotates or spins in the centrifuge 22. The spinning centrifuge bowl 30 separates the salvaged blood 200 into components according to the relative densities of the components. The red blood cells 202, which are the densest components of the blood, are propelled outward, against the circumferential wall 114 of the centrifuge bowl 30. The buffy coat 204 that contains other components, such as white blood cells and platelets, is arranged in the thin layer directly adjacent the concentrated mass of red blood cells 202. The plasma layer 206 is situated nearer the axis of rotation than the buffy coat 204 and includes a supernatant layer 208 that contains little fat and a fat layer 210 that is the least dense component of the salvaged blood 200 and situated in the plasma layer 206 nearest to the axis of rotation adjacent the supernatant layer 208.

At 302, some of the undesirable elements are removed from the centrifuge bowl during the fill phase. As the fill phase continues, more of the red blood cells 200 are pushed inwards, nearer to the axis of rotation. This pushes some of the fat layer 210 out of the collector 122 and the outlet chamber 124 at the top of the centrifuge bowl 30 and it pushes some of the fat layer 210 under the collector 122. The expelled portion of the fat layer 210 flows through the first waste line 64 connected to the outlet chamber 124, past the sensor 26, and through the second waste line 66 into the waste container 54. The portion of the fat layer 210 under the collector 122 remains trapped under the collector 122.

In some embodiments, as the fill phase further continues, more of the red blood cells 202 are pushed inwards, nearer to the axis of rotation, and some of the supernatant layer 208 is pushed out of the collector 122 and the outlet chamber 124 at the top of the centrifuge bowl 30. The expelled portion of the supernatant layer 208 flows through the first waste line 64 connected to the outlet chamber 124, past the sensor 26, and through the second waste line 66 into the waste container 54. The trapped portion of the fat layer 210 increases in size to substantially fill the area under the collector 122.

The sensor 26 senses when the buffy coat 204 begins to come out of the outlet chamber 124 or when the buffy coat 204 is at or near the top of the centrifuge bowl 30 and the sensor 26 provides a corresponding signal to the controller 28. In response to the signal from the sensor 26, the controller 28 stops the fill phase and the trapped portion of the fat layer 210 remains trapped under the collector 122. The autotransfusion system 20 provides further steps to remove the trapped portion of the fat layer 210 and reduce the amount of fat in the finished product.

At 304, the red blood cells 202 in the centrifuge bowl 30 are washed with the wash solution 220 in a first wash at a first wash speed to remove more of the undesirable components from the centrifuge bowl 30. In the first wash, the controller 28 controls the centrifuge bowl 30 and the pump 24 to wash the red blood cells 202 in the centrifuge bowl 30 at a slower first wash speed. The controller 28 spins the centrifuge bowl 30 and controls the pump 24 to pump the wash solution 220 into the centrifuge bowl 30 through the inlet tube 108. In some embodiments, the slower first wash speed is achieved by adjusting one or more of the flow rate of the wash solution 220 and the rotational speed of the centrifuge bowl 30.

In the first wash, the wash solution 220 enters the centrifuge bowl 30 through the inlet tube 108 and flows into the separation chamber 110, where it is separated from the red blood cells 202. As the first wash continues, the wash solution 220 is pushed inwards, nearer to the axis of rotation, and the less dense supernatant layer 208 is pushed out of the collector 122 and the outlet chamber 124 at the top of the centrifuge bowl 30. The expelled supernatant layer 208 flows through the first waste line 64 connected to the outlet chamber 124, past the sensor 26, and through the second waste line 66 into the waste container 54. The first wash removes more of the supernatant layer 208. The trapped portion of the fat layer 210 under the collector 122 remains substantially unaffected by the wash solution 220 in the first wash.

At 306, the red blood cells 202 in the centrifuge bowl 30 are washed with the wash solution 220 in a second wash at a second wash speed that is greater than the first wash speed to remove the trapped undesirable elements, such as the trapped fat layer 210, from the centrifuge bowl 30. In the second wash, the controller 28 controls the centrifuge bowl 30 and the pump 24 to wash the red blood cells 202 in the centrifuge bowl 30 in the second wash at a second wash speed that is faster than the slower first wash speed. The controller 28 spins the centrifuge bowl 30 and controls the pump 24 to pump the wash solution 220 into the centrifuge bowl 30 through the inlet tube 108.

The wash solution 220 is forced down through the inlet tube 108 and up through the central tube 222 of the centrifuge bowl 30. The second wash removes the trapped portion of the fat layer 210 from under the collector 122, where the wash solution 220 pushes the trapped portion of the fat layer 210 out of the collector 122 and the outlet chamber 124 at the top of the centrifuge bowl 30. The expelled portion of the fat layer 210 flows through the first waste line 64 connected to the outlet chamber 124, past the sensor 26, and through the second waste line 66 into the waste container 54. In some embodiments, the faster second wash speed is achieved by adjusting one or more of the flow rate of the wash solution 220 and the rotational speed of the centrifuge bowl 30.

At 308, the concentrated red blood cells 202 are mixed with the wash solution to provide diluted blood in the centrifuge bowl 30. After the two part wash phase, the controller 28 controls the centrifuge bowl 30 and the pump 24 to mix the concentrated red blood cells 202 and the wash solution 220 in the centrifuge bowl 30 to provide the diluted red blood cell mixture 224. In the centrifuge bowl 30, the diluted red blood cell mixture 224 is in at least the separation chamber 110 and the central tube 222. The diluted red blood cell mixture 224 has a lower HCT value than the final product 228 (shown in FIG. 14). In some embodiments, the controller 28 stops the centrifuge bowl 30 from spinning and the controller 28 stops the pump 24 to mix the concentrated red blood cells 202 and the wash solution 220 and provide the diluted red blood cell mixture 224.

Figure 16:
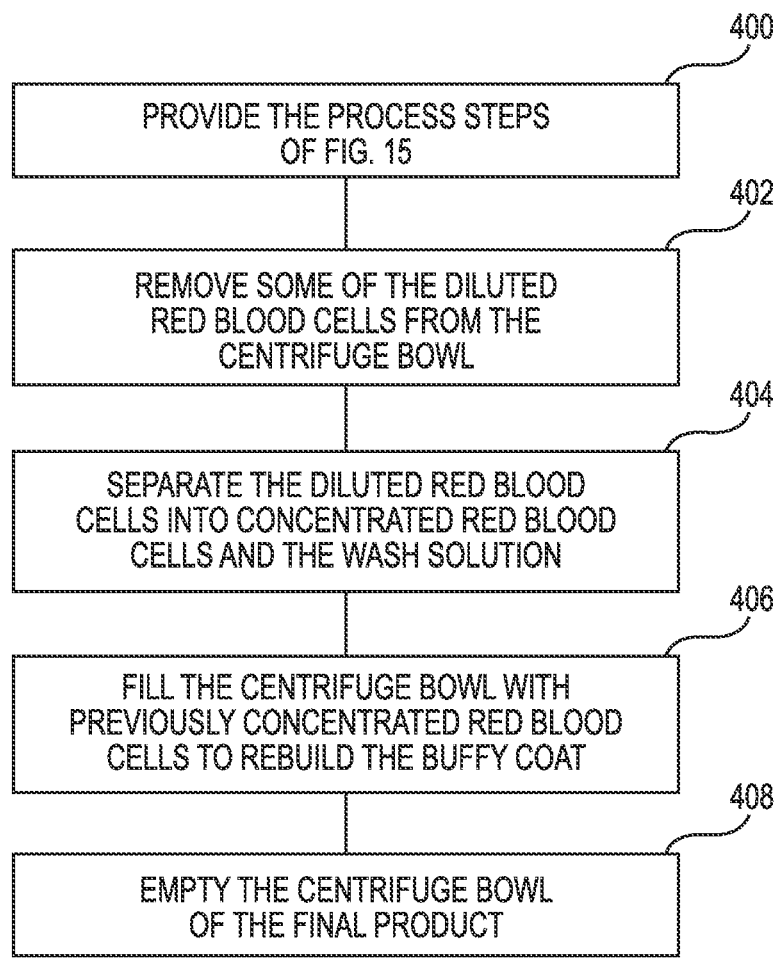
FIG. 16 is a flow chart diagram illustrating a consequent method for removing undesirable elements from salvaged blood, according to some embodiments described in the disclosure.

FIG. 16 is a flow chart diagram illustrating a consequent method for removing undesirable elements from the salvaged blood 200, according to some embodiments described in the disclosure. At 400, each of the process steps at 300, 302, 304, 306, and 308 of FIG. 15 are provided by the autotransfusion system 20, which then takes further steps to remove the wash solution 220 from the diluted red blood cell mixture 224 and provide the final product 228.

At 402, some of the diluted red blood cell mixture 224 is removed from the centrifuge bowl 30. After mixing the concentrated red blood cells 202 and the wash solution 220, a small quantity of the diluted red blood cell mixture 224 is drawn off to restore air balance in the centrifuge bowl 30. In some embodiments, some of the diluted red blood cell mixture 224 is pumped out of the centrifuge bowl 30 through the inlet tube 108 by the pump 24. In some embodiments, the diluted red blood cell mixture 224 that is pumped out of the centrifuge bowl 30 is stored in a diluted red blood cell container (not shown). In some embodiments, about 50 milliliters of the diluted red blood cell mixture 224 is drawn off to restore air balance in the centrifuge bowl 30.

At 404, the diluted red blood cell mixture 224 in the centrifuge bowl 30 is separated into concentrated red blood cells 202 and the wash solution 220. After removing some of the diluted red blood cell mixture 224, the controller 28 restarts the centrifuge 22 to spin the centrifuge bowl 30 and separate the diluted red blood cell mixture 224 into concentrated red blood cells 202 and the wash solution 220.

At 406, the centrifuge bowl 30 is filled with the previously concentrated red blood cells 226 to rebuild the buffy coat 204. As the previously concentrated red blood cells 226 are pumped into the centrifuge bowl 30, the centrifuge bowl 30 spins to separate the components into the red blood cells 202 and 226 and the wash solution 220. As more of the red blood cells 202 and 226 are pushed inwards, nearer to the axis of rotation, the wash solution 220 is pushed out of the collector 122 and the outlet chamber 124 at the top of the centrifuge bowl 30. The expelled portion of the wash solution 220 flows through the first waste line 64 connected to the outlet chamber 124, past the sensor 26, and through the second waste line 66 and into the waste container 54. The sensor 26 senses when the buffy coat 204 begins to come out of the outlet or when the buffy coat 204 is at or near the top of the centrifuge bowl 30 and the sensor 26 provides a corresponding signal to the controller 28. In response to the signal from the sensor 26, the controller 28 stops refilling the centrifuge bowl 30 with the previously concentrated red blood cells 226. After rebuilding the buffy coat 204, the centrifuge bowl 30 includes the red blood cells 202 and 226, at least some of the buffy coat 204, and possibly some of the wash solution 220. The autotransfusion system 20 proceeds to the emptying phase.

At 408, the centrifuge bowl 30 is emptied of the final product 228 that includes the concentrated red blood cells 202 and the previously concentrated red blood cells 226. In the emptying phase, the final product 228 that includes the concentrated red blood cells 202 and the previously concentrated red blood cells 226, is pumped out of the centrifuge bowl 30 through the inlet tube 108 and the collection valve 52 and into the collection bag 50. The final product 228 in the collection bag 50 includes the concentrated red blood cells 202 and the previously concentrated red blood cells 226 that were pumped out of the centrifuge bowl 30. This final product 228 can be used for reinfusion back to the patient via outlet line 74.

The autotransfusion system 20 provides a final product 228 that includes concentrated red blood cells 202 and 226 with a higher HCT value and a lower concentration of fat than obtained in other systems.

FIG. 17 is a table 500 illustrating test results obtained using the autotransfusion system 20 and some other autotransfusion systems, according to some embodiments described in the disclosure. The first four rows 502 show the test results obtained using a previous autotransfusion system and a centrifuge bowl similar to centrifuge bowl 30. In the first four rows 502, different centrifuge bowl sizes, indicated at 504, are used, including 55, 125, 175, and 225 bowls. The fifth row 506 shows the test results obtained using an autotransfusion system that includes a centrifuge bowl that is dissimilar to the centrifuge bowl 30, and referred to as an H225 bowl. The last four rows 508 show the test results obtained using the autotransfusion system 20 and the centrifuge bowl 30 in different bowl sizes, including 55, 125, 175, and 225 bowls. All samples of the inlet blood 510 have a percentage oil volume 512 of 4 percent.

As shown at 514, the percentage of oil volume in the collected red blood cells of the first four rows 502 is in a range from 2.38 to 6.39 percent, the percentage of oil volume in the collected red blood cells of the fifth row 506 is 3.57 percent, and the percentage of oil volume in the collected red blood cells of the last four rows 508 is in a range from 0.11 to 0.55 percent.

The oil volume ratio 516 in the first four rows 502 of the previous autotransfusion system using a centrifuge bowl similar to centrifuge bowl 30 compared to the autotransfusion system 20 and the centrifuge bowl 30 ranges from 10.95 to 24.74. Also, the oil volume ratio 516 in the fifth row 506 of the autotransfusion system using a different centrifuge bowl that is dissimilar to the centrifuge bowl 30 compared to the autotransfusion system 20 and the centrifuge bowl 30 is 32.67. Thus, the fat in the final product 228 obtained using the autotransfusion system 20 and the centrifuge bowl 30 is about 11 to 25 times less than the fat in the final product of the previous autotransfusion system using a centrifuge bowl similar to centrifuge bowl 30 and about 33 times less than the fat in the final product obtained using the autotransfusion system using a different centrifuge bowl that is dissimilar to the centrifuge bowl 30.

As shown at 518, the percent of the red blood cells recovered by each of the systems is substantially similar, however, as shown at 520, the percent of oil removed using the autotransfusion system 20 and the centrifuge bowl 30 is much greater than the percent of oil removed using the other systems of the first four rows 502 and the fifth row 506. Also, as shown at 522, the processing time is only slightly increased using the autotransfusion system 20 and the centrifuge bowl 30 as compared to the systems of the first four rows 502.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system for removing undesirable elements from blood, comprising:
   a centrifuge bowl including a collector and configured to separate the blood into components including the undesirable elements according to relative densities of the components;
   a pump to provide a wash solution that washes the blood in the centrifuge bowl;
   a sensor disposed near an outlet of the centrifuge bowl to sense buffy coat elements; and
   a controller operatively connected to the centrifuge bowl and the pump, the controller programmed to control the centrifuge bowl and the pump to:
     add a first amount of the wash solution with the pump to wash the blood in the centrifuge bowl in a first wash step that has a first wash speed to remove a first portion of the undesirable elements,
     add a second amount of the wash solution with the pump to wash the blood in the centrifuge bowl in a second wash step that has a second wash speed that is adequate to remove a trapped portion of the undesirable elements that are trapped by the collector and to obtain a first concentrated blood component,
     mix the first concentrated blood component and a remaining amount of the first amount and the second amount of the wash solution in the centrifuge bowl with the centrifuge bowl to provide a diluted blood component,
     separate the diluted blood component into a second concentrated blood component and the remaining amount of the wash solution with the centrifuge bowl,
     fill the centrifuge bowl with a previously concentrated blood component from a container with the pump to build a buffy coat, and
     empty the centrifuge bowl of the second concentrated blood component and the previously concentrated blood component from the container with the pump after the buffy coat is reached.

2. The system of claim 1, wherein the controller further controls the pump to fill the centrifuge bowl with the blood and the centrifuge bowl to separate the blood into the components according to the relative densities of the components prior to the first wash step.

3. The system of claim 2, wherein the controller further controls the centrifuge bowl and the pump to remove a pre-wash portion of the undesirable elements prior to the first wash step.

4. The system of claim 1, wherein the controller controls at least one of the centrifuge bowl and the pump to provide the first wash speed in the first wash step and the second wash speed in the second wash step, such that the second wash speed is greater than the first wash speed to remove the trapped portion of the undesirable elements from the centrifuge bowl.

5. The system of claim 1, wherein the centrifuge bowl includes a central tube such that the central tube is filled with air in the first wash step and the wash solution in the second wash step flows through the central tube to remove the trapped portion of the undesirable elements from the centrifuge bowl.

6. The system of claim 1, wherein the controller stops at least one of the centrifuge bowl from spinning and the pump to mix the blood and the remaining amount of the first amount and the second amount of the wash solution in the centrifuge bowl and provides the diluted blood component.

7. The system of claim 5, wherein the controller further controls the pump to remove a portion of the diluted blood component from the centrifuge bowl and restore air balance to the central tube after the second wash step and prior to separating the diluted blood component.

8. The system of claim 1, wherein the trapped portion of the undesirable elements includes fat.

9. A system for removing undesirable elements from blood, comprising:
a centrifuge bowl including a collector and configured to separate the blood into components according to relative densities of the components;
a pump to provide a wash solution that washes the blood in the centrifuge bowl; and
a controller operatively connected to the centrifuge bowl and the pump and programmed to control the centrifuge bowl and the pump to wash the blood in the centrifuge bowl in a first wash step at a first wash speed to remove a first wash portion of the undesirable components and to wash the blood in the centrifuge bowl in a second wash step at a second wash speed that is greater than the first wash speed and adequate to remove a trapped portion of the undesirable elements that are trapped by the collector from the centrifuge bowl to provide a first concentrated blood component immediately after the second wash step, and programmed to control the centrifuge bowl and the pump to mix the first concentrated blood component and the wash solution in the centrifuge bowl to provide a diluted blood component.

10. The system of claim 9, wherein the controller stops at least one of the centrifuge bowl from spinning and the pump to mix the first concentrated blood component and the wash solution in the centrifuge bowl to provide the diluted blood component.

11. The system of claim 9, wherein the controller further controls the pump to remove a portion of the diluted blood component from the centrifuge bowl and the centrifuge bowl to separate the diluted blood component in the centrifuge bowl into a second concentrated blood component and the wash solution.

12. The system of claim 11, wherein the controller further controls the pump to fill the centrifuge bowl with a previously concentrated blood component from a container to build a buffy coat and to empty the centrifuge bowl of the second concentrated blood component and the previously concentrated blood component from the container after a sensor disposed near a centrifuge bowl outlet senses the buffy coat.

13. The system of claim 9, wherein the centrifuge bowl includes a central tube and the wash solution in the second wash step flows through the central tube to remove the trapped portion of the undesirable elements from under the collector.

14. A system for removing undesirable elements from blood, comprising:
a centrifuge bowl including a top and a collector and configured to separate the blood into components according to relative densities of the components;
a pump to provide a wash solution that washes the blood in the centrifuge bowl;
a sensor to sense at least one of a buffy coat coming out of the centrifuge bowl and the buffy coat at or near the top of the centrifuge bowl; and
a controller operatively connected to the centrifuge bowl and the pump and programmed to control the centrifuge bowl and the pump to add a first amount of the wash solution to wash the blood in the centrifuge bowl with the pump in a first wash step that has a first wash speed that removes a first portion of the undesirable elements and to add a second amount of the wash solution to wash the blood in the centrifuge bowl with the pump in a second wash step that has a second wash speed that is adequate to remove a trapped portion of the undesirable elements trapped by the collector and to obtain a first concentrated blood component, the controller further programmed to control the centrifuge bowl and the pump to mix the first concentrated blood component and a remaining amount of the first amount and the second amount of the wash solution in the centrifuge bowl with the centrifuge bowl to provide a diluted blood component, separate the diluted blood component into a second concentrated blood component and the remaining amount of the wash solution with the centrifuge bowl, begin filling the centrifuge bowl with a previously concentrated blood component from a container with the pump to build the buffy coat, stop filling the centrifuge bowl with the previously concentrated blood from the container with the pump in response to receiving a signal from the sensor that indicates the buffy coat has been sensed, and empty the centrifuge bowl of the second concentrated blood component and the previously concentrated blood component from the container with the pump after the buffy coat has been sensed.

* * * * *